United States Patent [19]

Zellers et al.

[11] 4,186,061
[45] Jan. 29, 1980

[54] FRACTIONATION OF METHYL-MERCAPTAN REACTOR EFFLUENT

[75] Inventors: Dale A. Zellers; Joseph W. Clark, both of Bartlesville, Okla.

[73] Assignee: Phillips Petroleum Company, Bartlesville, Okla.

[21] Appl. No.: 809,831

[22] Filed: Jun. 24, 1977

[51] Int. Cl.² .................................... C07C 148/04
[52] U.S. Cl. .................................... 203/96; 203/3; 203/DIG. 19; 260/609 C; 55/68; 55/70
[58] Field of Search ............. 203/96, 92, 95, 97, 203/93, 76, 79, 83, 85, DIG. 19, 99, 39, 3; 260/609 R, 609 C; 55/68, 73

[56] References Cited

U.S. PATENT DOCUMENTS

| | | | |
|---|---|---|---|
| 2,309,654 | 2/1943 | Leum et al. | 260/609 C |
| 2,455,656 | 12/1948 | Cauley | 260/609 C |
| 2,797,191 | 6/1957 | Jarboe et al. | 203/96 |
| 2,822,400 | 2/1958 | Cinque et al. | 260/609 R |
| 3,697,602 | 10/1972 | Schreyer et al. | 260/609 R |
| 3,792,094 | 2/1974 | Hanson | 260/609 R |

Primary Examiner—Wilbur L. Bascomb, Jr.

[57] ABSTRACT

A method for separating a feedstock comprising hydrogen sulfide, methyl mercaptan, methanol, and water in which a sufficient amount of water is injected into the fractionating column above the feedstock inlet to water wash the organic phase, decanting water and methanol from a tray below the feedstock inlet so that the stream comprising hydrogen sulfide and a minimum of water can be removed overhead and a stream comprising methyl mercaptan and a minimum of water can be removed as bottoms.

3 Claims, 1 Drawing Figure

SEPARATION OF H₂S, METHANOL AND METHYL MERCAPTAN BY EXTRACTIVE DISTILLATION WITH WATER

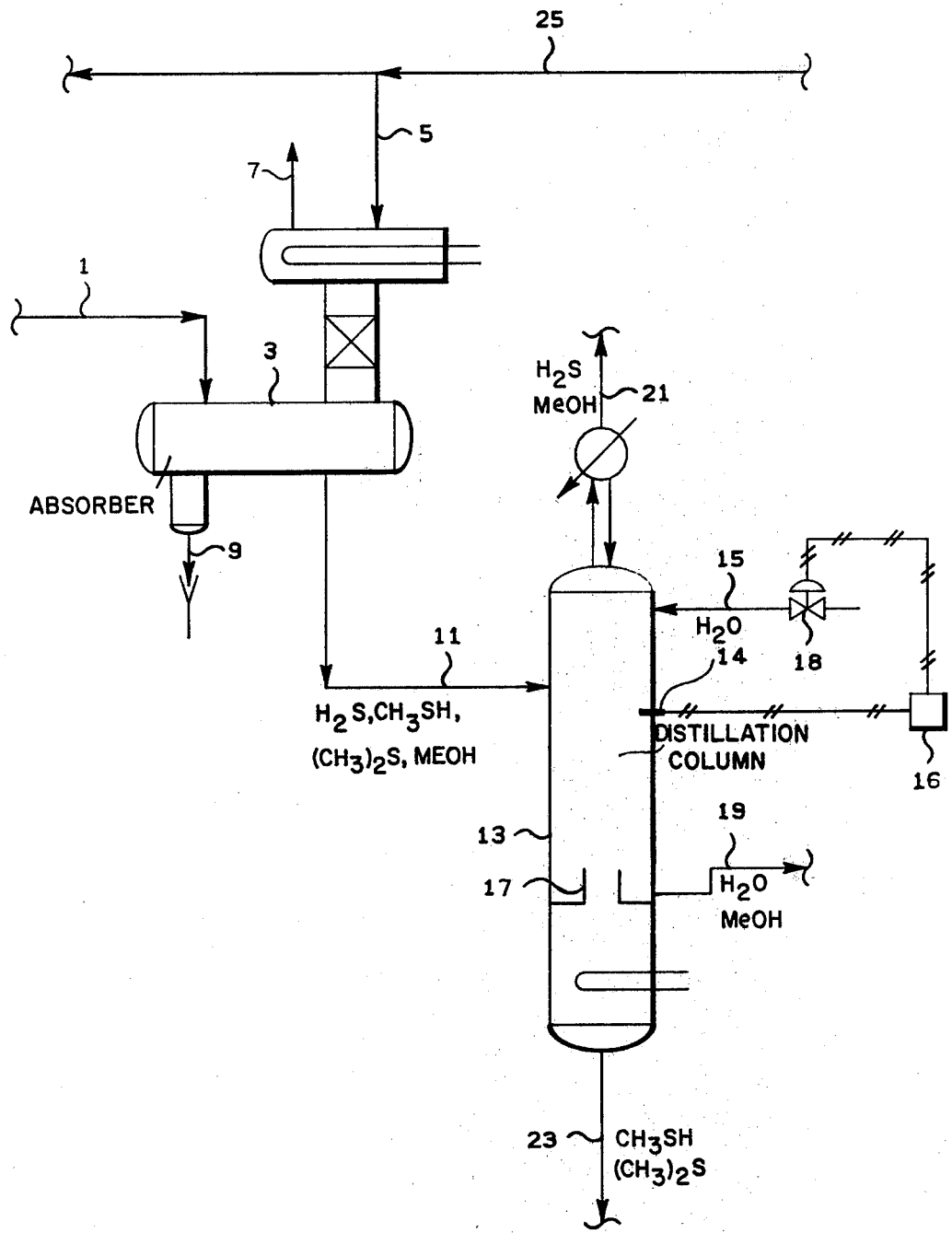
SEPARATION OF H₂S, METHANOL AND
METHYL MERCAPTAN BY EXTRACTIVE
DISTILLATION WITH WATER

FRACTIONATION OF METHYL-MERCAPTAN REACTOR EFFLUENT

BACKGROUND OF THE INVENTION

This invention relates to fractionation. In one of its aspects this invention relates to the fractionation of a mercaptan-containing stream containing both methanol and water. In another of its aspects this invention relates to fractionation apparatus. In still another of its aspects this invention relates to fractionation procedures to obtain overhead and bottoms streams from the fractionation containing a minimum of water.

The usual commercial processes for producing methyl mercaptan, whether using hydrogen sulfide and methanol as reactants as in U.S. Pat. Nos. 2,822,400 and 3,792,094 or in a combination process in which there is a reaction of carbon disulfide and hydrogen and a reaction of hydrogen sulfide and methanol, produce a reactor effluent containing both water and unreacted methanol along with the desired methyl mercaptan product and unreacted hydrogen sulfide. To remove the hydrogen sulfide, the reactor effluent is subjected to a fractionation. The presence of methanol changes the solubility of water in the organic phase in such a manner that the fractionation to strip hydrogen sulfide from the effluent cannot be operated so that dry overhead comprising hydrogen sulfide and a dry bottoms product comprising methyl mercaptan can be obtained. A method for manipulating the fractionation of an effluent stream containing hydrogen sulfide, methyl mercaptan, methanol, and water has now been developed.

It is therefore an object of this invention to provide a method for separating a feedstock comprising hydrogen sulfide, methyl mercaptan, methanol, and water to obtain a minimum of water in the overhead and bottoms streams from the fractionation process. It is also an object of this invention to provide an apparatus by which such a separation can be accomplished.

Other aspects, objects, and the various advantages of this invention will become apparent upon study of this specification, the drawing, and the appended claims.

STATEMENT OF THE INVENTION

A method is provided for separating a feedstock comprising hydrogen sulfide, methyl mercaptan, methanol, and water to obtain a minimum of water in the overhead and bottoms streams from the fractionation. The method comprises introducing the feedstock into a fractionating column having a heated kettle and cooled overhead; introducing sufficient water into the fractionating column above the feedstock inlet to maintain a molal ratio of water to methanol of at least 10:1 in the fractionator between the water inlet and the section of the fractionating column from which water and methanol are decanted; decanting water and methanol from the fractionator from a collecting and decanting section below the feedstock inlet; removing as overhead from the fractionator a stream comprising hydrogen sulfide and a minimum of water; and removing from the fractionator as bottoms a stream comprising methyl mercaptan and a minimum of water.

In one embodiment of the invention an apparatus is provided for separating a feedstock comprising hydrogen sulfide, methyl mercaptan, methanol, and water. The apparatus is a fractionator with heating means for the kettle and cooling means for the overhead which has an inlet means for feedstock in the mid-portion of the fractionator, an inlet means for water above the feedstock inlet means, and a means below the feedstock inlet means for collecting and decanting methanol and water from the fractionator. There are also means for removing an overhead stream and means for removing a bottoms stream from the fractionator.

The operation of this invention depends, in its method, on the introduction of sufficient water into the fractionating column above the feedstock inlet to maintain a molal ratio of water to methanol of at least 10:1 in the fractionator as measured in the space between the water inlet and the section from which water and methanol are decanted. In a preferred embodiment the molal ratio of water to methanol is maintained in the range of about 10:1 to about 20:1. The apparatus of the invention is dependent upon the comparative spacing of the inlet means for the feedstock, the inlet means for water and the means by which methanol and water are collected and decanted from the fractionator. Means for collecting and decanting from a fractionator are well known in the art and can be described as any variation of a tray-like structure upon which methanol-water mixture can be collected and from which there is an opening through which the mixture can pass from the fractionator to a collecting line outside the fractionator.

The operation and apparatus of this invention can best be understood when studied in conjunction with the drawing of this invention which is a line flow diagram of a process in which a reactor effluent having hydrogen sulfide, methyl mercaptan, methanol, and water is separated into component streams.

Referring now to the drawing, reactor effluent from a process for producing methyl mercaptan, in this case the reaction of hydrogen sulfide with methanol, is passed through line 1 into an absorber-separator 3 into which is also passed from line 5 a stream comprising predominantly dimethyl sulfide as absorbent. The absorbent passes countercurrently with vapors from the separator-absorber 3 to absorb hydrocarbons from the vapors so that the absorber overhead stream passed through line 7 is predominantly light gases such as hydrogen, carbon monoxide, methane, and carbon dioxide. In the separator portion of the absorber-separator 3 some of the water in the reactor effluent is trapped and removed through line 9 while the hydrocarbon mixture containing the methyl mercaptan product, dimethyl sulfide absorbent, absorbed hydrogen sulfide, methanol, and water, among other compounds, is transferred through the absorber bottoms line 11 as feed for the extractive stripper 13 of this invention.

In the extractive stripper 13, water is fed into the upper portion of the fractionator column at a point above the point of entry of the feedstock. The water serves to wash methanol from the organic mixture in the fractionator and the water and methanol are collected as a separate phase from the organic liquid phase in a collection section 17 and are removed through a water draw line 19. In this example the water collection section 17 is a weir tray on which water and absorbed methanol can collect to be removed by a side draw while organic liquids overflow the tray into the stripping section below. Sufficient water is introduced in the water feed 15 to provide a molal ratio of water to methanol in the column between the water feed 15 and the water draw 19 that is at least 10:1. This ratio of water to methanol allows scrubbing of the methanol from the organic liquid to produce stripped overhead through line 21 that may contain a negligible amount of water and allows a bottoms stream to be produced through line 23 that may contain water and/or methanol in negligible amounts.

The molal ratio of water to methanol can be determined by an automatic analysis system from a sample taken by a probe 14 located between the water inlet and the water draw. A signal can be generated by a control means 16, such as an analyzer controller, in response to the analysed metal ratio with the signal automatically controlling the setting of the valve 18 on line 15 admitting water to fractionator 13.

The stripper bottoms stream which is predominantly methyl mercaptan and dimethyl sulfide is further treated to produce a dry methyl mercaptan product and a dimethyl sulfide stream, which can be further purified as product or recycled through line 25 to be used partially as absorbent passed through line 5 into the stripper absorber 3 and partially as recycle to the reactor. The remainder of the dimethyl mercaptan stream is further treated to produce a purified dimethyl sulfide stream from which heavies have been removed.

The following is a material balance for a typical flow through the parts of the system illustrated in the drawing showing the amounts of various constituents in Kg Mols/Hr.

| MATERIAL BALANCE, Kg Mols/Hr | | | | | | | | | |
|---|---|---|---|---|---|---|---|---|---|
| | 1 | 5 | 7 | 9 | 11 | 21 | 15 | 19 | 23 | 25 |
| | Reactor Effluent | DMS to Absorber | Absorber Overhead | Absorber Water Discharge | Absorber Bottoms | Stripper Overhead | $H_2O$ Feed to Stripper | Stripper Water Draw | Stripper Bottoms | DMS Recycle |
| $H_2$ | 8.0 | | 3.2 | | 4.8 | 4.8 | | | | |
| CO | 10.5 | | 1.1 | | 9.4 | 9.4 | | | | |
| $CH_4$ | 14.9 | | 2.1 | | 12.8 | 12.8 | | | | |
| $CO_2$ | 26.4 | | 1.7 | | 24.7 | 24.7 | | | | |
| $H_2S$ | 432.0 | | 0.1 | | 431.9 | 431.7 | | 0.2 | | |
| COS | 3.0 | | | 0.5 | 2.5 | 2.3 | | 0.2 | | |
| $C_3H_8$ | 10.2 | | 0.3 | | 9.9 | 9.8 | | 0.1 | | |
| $C_4H_{10}$ | 1.2 | | | | 1.2 | 1.2 | | | | |
| $CH_3SH$ | 57.1 | 0.8 | | | 57.9 | 2.4 | | 1.5 | 54.0 | 0.9 |
| $(CH_3)_2S$ | 12.0 | 41.1 | 0.5 | | 52.6 | | | 0.3 | 52.3 | 46.5 |
| $CS_2$ | 0.4 | 0.6 | | | 1.0 | | | | 1.0 | 0.9 |
| $CH_3OH$ | 1.7 | | | 0.1 | 1.6 | 0.4 | | 1.2 | | |
| $(C_2H_5)_2S$ | 0.2 | 0.7 | | | 0.9 | | | | 0.9 | 0.8 |
| $H_2O$ | 33.6 | | | 19.1 | 14.5 | 0.1 | 17.6 | 32.0 | | |
| Total | 611.2 | 43.2 | 9.0 | 19.7 | 625.7 | 499.6 | 17.6 | 35.5 | 108.2 | 49.1 |

Typical operating conditions using the extractive stripper of this invention with a through flow as set forth above in the material balance are as follows:

| Column Pressure | 510 psia (3.52 mPa) |
|---|---|
| Top Tray Temperature | 118° F. (48° C.) |
| Liquid Feed | 121° F. (49.5° C.) |
| Temperature | |
| Weir Tray Temperature | 285° F. (141° C.) |
| Kettle Temperature | 331° F. (166° C.) |
| Reflux/Distillate molal ratio | 1.37 |
| Total Trays | 40 |

We claim:

1. A method for separating a feedstock comprising hydrogen sulfide, methyl mercaptan, methanol, and water to obtain minimum water in the overhead and bottoms streams, said method comprising:
   (a) introducing said feed stock into a fractional distillation column having a heated kettle and a cooled overhead;
   (b) introducing sufficient water into the column above the feedstock inlet to maintain a molal ratio of water to methanol of at least 10:1 in the distillation column between the water inlet and the point for water and methanol decanting;
   (c) decanting the water and methanol from the distillation column from a collecting and decanting section below the feedstock inlet;
   (d) removing from the distillation column an overhead stream comprising principally hydrogen sulfide; and
   (e) removing from the distillation column a bottoms stream comprising methyl mercaptan.

2. A method of claim 1 wherein the molal ratio of water to methanol is maintained in the range of about 10:1 to about 20:1.

3. A method of claim 1 wherein the feedstock also contains dimethyl sulfide and the bottoms stream contains dimethyl sulfide.

* * * * *